US008148157B2

(12) United States Patent
Backus et al.

(10) Patent No.: US 8,148,157 B2
(45) Date of Patent: Apr. 3, 2012

(54) REFERENCE, CALIBRATOR, OR CONTROL COMPOSITION OF PlGF-1 AND SFLT-1

(75) Inventors: John W. Backus, Ontario, NY (US); Jian Zheng, Raritan, NJ (US); George Bashirians, Penfield, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 407 days.

(21) Appl. No.: 12/349,695

(22) Filed: Jan. 7, 2009

(65) Prior Publication Data

US 2009/0176264 A1   Jul. 9, 2009

Related U.S. Application Data

(60) Provisional application No. 61/019,443, filed on Jan. 7, 2008.

(51) Int. Cl.
*G01N 31/00* (2006.01)
(52) U.S. Cl. .............................. 436/15; 435/15
(58) Field of Classification Search ............... 436/15; 435/15
See application file for complete search history.

(56) References Cited

U.S. PATENT DOCUMENTS

| 2005/0176634 A1 | 8/2005 | Maglione et al. | |
| 2007/0111326 A1* | 5/2007 | Sogin et al. | 436/518 |
| 2009/0082268 A1* | 3/2009 | Salvia | 514/12 |

FOREIGN PATENT DOCUMENTS

| WO | WO 92/06194 | 4/1992 |
| WO | WO 03/097688 A2 | 11/2003 |
| WO | WO 2006/069373 A2 | 6/2006 |
| WO | WO 2009/089271 A1 | 7/2009 |
| WO | WO 2009/155324 A2 | 12/2009 |

OTHER PUBLICATIONS

Errico M. et al. Indentification of Placenta Grwoth Factor Determinants for Binding and Activation of Flt-1 Receptor. J of Biological Chemistry 279(42)43929-39, Oct. 2004.*
Davis-Smyth et al., J Biol Chem 273(6):3216-3222 (1998).
Errico et al., J Biol Chem 279:43929-43939 (2004).
Hornig, Carsten et al., Release and Complex Formation of Soluble VEGFR-1 from Endothelial Cells and Biological Fluids, Laboratory Investigation, 2000, vol. 80, No. 4, p. 443-454.
Robinson, Christopher J. et al., Evaluation of Placenta Growth Factor and Soluble FMS-Like Tyrosine Kinase 1 Receptor Levels in Mild and Severe Preeclampsia, American Journal of Obstetrics and Gynecology, 2006, vol. 195, No. 1, p. 255-259.

* cited by examiner

*Primary Examiner* — Ralph Gitomer (57) ABSTRACT

Disclosed herein are compositions and methods comprising two or more proteins in which at least one of the proteins has been altered to reduce their mutual recognition and binding. Such compositions are useful as reference, calibrators or controls in methods and assays for determining the amount of one or more of the proteins that may be present in a sample of interest or in confirming the presence of one or more of the proteins in the sample. More particularly, it relates to compositions and methods comprising altered placental growth factor-1 (PlGF-1) and soluble fms-like tyrosine kinase (sFlt-1) and methods for determining the amount or confirming the presence of sFlt-1 and/or PlGF-1 in a sample of interest.

3 Claims, 2 Drawing Sheets

SEQUENCE LISTING

```
<160> NUMBER OF SEQ ID NOS: 8

<210> SEQ ID NO 1
<211> LENGTH: 132
<212> TYPE: PRT
<213> ORGANISM: Homo sapiens

<400> SEQUENCE: 1

Met Leu Pro Ala Val Pro Pro Gln Gln Trp Ala Leu Ser Ala Gly Asn
1               5                   10                  15

Gly Ser Ser Glu Val Glu Val Val Pro Phe Gln Glu Val Trp Gly Arg
                20                  25                  30

Ser Tyr Cys Arg Ala Leu Glu Arg Leu Val Asp Val Val Ser Glu Tyr
            35                  40                  45

Pro Ser Glu Val Glu His Met Phe Ser Pro Ser Cys Val Ser Leu Leu
    50                  55                  60

Arg Cys Thr Gly Cys Cys Gly Asp Glu Asn Leu His Cys Val Pro Val
65                  70                  75                  80

Glu Thr Ala Asn Val Thr Met Gln Leu Leu Lys Ile Arg Ser Gly Asp
                85                  90                  95

Arg Pro Ser Tyr Val Glu Leu Thr Phe Ser Gln His Val Arg Cys Glu
            100                 105                 110

Cys Arg Pro Leu Arg Glu Lys Met Lys Pro Glu Arg Cys Gly Asp Ala
        115                 120                 125

Val Pro Arg Arg
    130

<210> SEQ ID NO 2
<211> LENGTH: 21
<212> TYPE: PRT
<213> ORGANISM: Homo sapiens

<400> SEQUENCE: 2

Met Arg Gly Ser His His His His His His Gly Ser Gly Ser Gly Ser
1               5                   10                  15

Gly Ile Glu Gly Arg
            20

<210> SEQ ID NO 3
<211> LENGTH: 129
<212> TYPE: PRT
<213> ORGANISM: Homo sapiens

<400> SEQUENCE: 3

Ala Val Pro Pro Gln Gln Trp Ala Leu Ser Ala Gly Asn Gly Ser Ser
1               5                   10                  15

Glu Val Glu Val Val Pro Phe Gln Glu Val Trp Gly Arg Ser Tyr Cys
                20                  25                  30

Arg Ala Leu Glu Arg Leu Val Asp Val Val Ser Glu Tyr Pro Ser Glu
            35                  40                  45

Val Glu His Met Phe Ser Pro Ser Cys Val Ser Leu Leu Arg Cys Thr
    50                  55                  60
```

```
Gly Cys Cys Gly Asp Glu Asn Leu His Cys Val Pro Val Glu Thr Ala
 65                  70                  75                  80

Asn Val Thr Met Gln Leu Leu Lys Ile Arg Ser Gly Asp Arg Pro Ser
                 85                  90                  95

Tyr Val Glu Leu Thr Phe Ser Gln His Val Arg Cys Glu Cys Arg Pro
                100                 105                 110

Leu Arg Glu Lys Met Lys Pro Glu Arg Cys Gly Asp Ala Val Pro Arg
            115                 120                 125

Arg

<210> SEQ ID NO 4
<211> LENGTH: 129
<212> TYPE: PRT
<213> ORGANISM: Homo sapiens

<400> SEQUENCE: 4

Ala Val Pro Pro Gln Gln Trp Ala Leu Ser Ala Gly Asn Gly Ser Ser
 1               5                  10                  15

Glu Val Glu Val Val Pro Phe Gln Glu Val Trp Gly Arg Ser Tyr Cys
                 20                  25                  30

Arg Ala Leu Glu Arg Leu Val Asp Val Val Ser Glu Tyr Pro Ser Glu
             35                  40                  45

Val Glu His Met Phe Ser Pro Ser Cys Val Ser Leu Leu Arg Cys Thr
 50                  55                  60

Gly Cys Cys Gly Ala Ala Asn Leu His Cys Val Pro Val Glu Thr Ala
 65                  70                  75                  80

Asn Val Thr Met Gln Leu Leu Lys Ile Arg Ser Gly Asp Arg Pro Ser
                 85                  90                  95

Tyr Val Glu Leu Thr Phe Ser Gln His Val Arg Cys Glu Cys Arg Pro
                100                 105                 110

Leu Arg Glu Lys Met Lys Pro Glu Arg Cys Gly Asp Ala Val Pro Arg
            115                 120                 125

Arg

<210> SEQ ID NO 5
<211> LENGTH: 687
<212> TYPE: PRT
<213> ORGANISM: Homo sapiens

<400> SEQUENCE: 5

Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Lys Leu Lys Asp Pro
                 20                  25                  30

Glu Leu Ser Leu Lys Gly Thr Gln His Ile Met Gln Ala Gly Gln Thr
             35                  40                  45

Leu His Leu Gln Cys Arg Gly Glu Ala Ala His Lys Trp Ser Leu Pro
 50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
                100                 105                 110

Pro Thr Ser Lys Lys Lys Glu Thr Glu Ser Ala Ile Tyr Ile Phe Ile
            115                 120                 125
```

```
Ser Asp Thr Gly Arg Pro Phe Val Glu Met Tyr Ser Glu Ile Pro Glu
130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
            180                 185                 190
Ile Ile Ser Asn Ala Thr Tyr Lys Glu Ile Gly Leu Leu Thr Cys Glu
        195                 200                 205
Ala Thr Val Asn Gly His Leu Tyr Lys Thr Asn Tyr Leu Thr His Arg
210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
        355                 360                 365
Trp Leu Lys Asp Gly Leu Pro Ala Thr Glu Lys Ser Ala Arg Tyr Leu
370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
        435                 440                 445
Arg Gln Ile Leu Thr Cys Thr Ala Tyr Gly Ile Pro Gln Pro Thr Ile
450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
        515                 520                 525
Ile Ser Gly Ile Tyr Ile Cys Ile Ala Ser Asn Lys Val Gly Thr Val
530                 535                 540
Gly Arg Asn Ile Ser Phe Tyr Ile Thr Asp Val Pro Asn Gly Phe His
545                 550                 555                 560
```

```
Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
            595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
                660                 665                 670

Lys Ser Thr Arg Asn Asp Cys Thr Thr Gln Ser Asn Val Lys His
                675                 680                 685
```

<210> SEQ ID NO 6
<211> LENGTH: 142
<212> TYPE: PRT
<213> ORGANISM: Homo sapiens

<400> SEQUENCE: 6

```
Met Arg Gly Ser Ala Val Pro Pro Gln Gln Trp Ala Leu Ser Ala Gly
1               5                   10                  15

Asn Gly Ser Ser Glu Val Glu Val Val Pro Phe Gln Glu Val Trp Gly
                20                  25                  30

Arg Ser Tyr Cys Arg Ala Leu Glu Arg Leu Val Asp Val Val Ser Glu
            35                  40                  45

Tyr Pro Ser Glu Val Glu His Met Phe Ser Pro Ser Cys Val Ser Leu
        50                  55                  60

Leu Arg Cys Thr Gly Cys Cys Gly Asp Glu Asn Leu His Cys Val Pro
65                  70                  75                  80

Val Glu Thr Ala Asn Val Thr Met Gln Leu Leu Lys Ile Arg Ser Gly
                85                  90                  95

Asp Arg Pro Ser Tyr Val Glu Leu Thr Phe Ser Gln His Val Arg Cys
                100                 105                 110

Glu Cys Arg Pro Leu Arg Glu Lys Met Lys Pro Glu Arg Cys Gly Asp
            115                 120                 125

Ala Val Gly Pro Gly Gln Ile Val Gly Gly Val Tyr Leu Leu
        130                 135                 140
```

<210> SEQ ID NO 7
<211> LENGTH: 142
<212> TYPE: PRT
<213> ORGANISM: Homo sapiens

<400> SEQUENCE: 7

```
Met Arg Gly Ser Ala Val Pro Pro Gln Gln Trp Ala Leu Ser Ala Gly
1               5                   10                  15

Asn Gly Ser Ser Glu Val Glu Val Val Pro Phe Gln Glu Val Trp Gly
                20                  25                  30

Arg Ser Tyr Cys Arg Ala Leu Glu Arg Leu Val Asp Val Val Ser Glu
            35                  40                  45

Tyr Pro Ser Glu Val Glu His Met Phe Ser Pro Ser Cys Val Ser Leu
        50                  55                  60
```

```
Leu Arg Cys Thr Gly Cys Cys Gly Ala Ala Asn Leu His Cys Val Pro
 65                  70                  75                  80

Val Glu Thr Ala Asn Val Thr Met Gln Leu Leu Lys Ile Arg Ser Gly
                 85                  90                  95

Asp Arg Pro Ser Tyr Val Glu Leu Thr Phe Ser Gln His Val Arg Cys
                100                 105                 110

Glu Cys Arg Pro Leu Arg Glu Lys Met Lys Pro Glu Arg Cys Gly Asp
            115                 120                 125

Ala Val Gly Pro Gly Gln Ile Val Gly Gly Val Tyr Leu Leu
        130                 135                 140

<210> SEQ ID NO 8
<211> LENGTH: 142
<212> TYPE: PRT
<213> ORGANISM: Homo sapiens

<400> SEQUENCE: 8

Met Arg Gly Ser Ala Val Pro Pro Gln Gln Trp Ala Leu Ser Ala Gly
  1               5                  10                  15

Asn Gly Ser Ser Glu Val Glu Val Val Pro Phe Gln Glu Val Trp Gly
                 20                  25                  30

Arg Ser Tyr Cys Arg Ala Leu Glu Arg Leu Val Asp Val Val Ser Glu
             35                  40                  45

Tyr Pro Ser Glu Val Glu His Met Phe Ser Pro Ser Cys Val Ser Leu
 50                  55                  60

Leu Arg Cys Thr Gly Cys Gly Gly Ala Ala Asn Leu His Cys Val Pro
 65                  70                  75                  80

Val Glu Thr Ala Asn Val Thr Met Gln Leu Leu Lys Ile Arg Ser Gly
                 85                  90                  95

Asp Arg Pro Ser Tyr Val Glu Leu Thr Phe Ser Gln His Val Arg Cys
                100                 105                 110

Glu Cys Arg Pro Leu Arg Glu Lys Met Lys Pro Glu Arg Cys Gly Asp
            115                 120                 125

Ala Val Gly Pro Gly Gln Ile Val Gly Gly Val Tyr Leu Leu
        130                 135                 140
```

REFERENCE, CALIBRATOR, OR CONTROL COMPOSITION OF PlGF-1 AND SFLT-1

CROSS-REFERENCE TO RELATED APPLICATIONS

This application claims the benefit of U.S. Provisional Application No. 61/019,443, filed Jan. 7, 2008.

FIELD OF THE INVENTION

The present invention relates to compositions and methods comprising two or more proteins altered to prevent their mutual recognition and binding. The compositions can be used as reference, calibrator or control in analytical assays capable of detecting both altered and unaltered or native forms of one or more of the proteins.

BACKGROUND OF THE INVENTION

Pre-eclampsia is a syndrome of hypertension, edema, and proteinuria that affects 5 to 10% of pregnancies and results in substantial maternal and fetal morbidity and mortality. Pre-eclampsia accounts for at least 200,000 maternal deaths worldwide per year. The symptoms of pre-eclampsia typically appear after the 20$^{th}$ week of pregnancy.

Development of a fetus and placenta is mediated by several growth factors. Vascular endothelial growth factor (VEGF) is an endothelial cell-specific mitogen, and angiogenic inducer. VEGF mediates vascular permeability and has been shown to be involved in glomerular capillary repair. VEGF binds as a homodimer to one of two homologous membrane-spanning receptor tyrosine kinases, the fms-like tyrosine kinase (Flt-1) and the kinase domain receptor (KDR).

Placental growth factor (PlGF) is a VEGF family member that is also involved in placental development. PlGF is expressed by cytotrophoblasts and syncytiotrophoblasts and is capable of inducing proliferation, migration, and activation of endothelial cells. PlGF binds as a homodimer to the Flt-1 receptor, but not the KDR receptor. Both PlGF and VEGF contribute to the mitogenic activity and angiogenesis that are critical for the developing placenta.

A soluble form of the Flt-1 receptor (sFlt-1) has been identified in a cultured medium of human umbilical vein endothelial cells and in vivo expression was subsequently demonstrated in placental tissue. sFlt-1 is a splice variant of the Flt-1 receptor which lacks the transmembrane and cytoplasmic domains. sFlt-1 binds to VEGF with high affinity but does not stimulate mitogenesis of endothelial cells. sFlt-1 is believed to act as a "physiologic sink" to down-regulate VEGF signaling pathways. Regulation of sFlt-1 levels therefore works to modulate VEGF and VEGF signaling pathways. Careful regulation of VEGF and PlGF signaling pathways is critical for maintaining appropriate proliferation, migration, and angiogenesis by trophoblast cells in the developing placenta.

A single gene codes for human PlGF. However, splicing of the mature PlGF mRNA results in three different length isoforms: PlGF-1 (PlGF131), PlGF-2 (PlGF152), and PlGF-3 (PlGF203). Another variant, PlGF-4, has been reported (Yang, et al, J Reprod Immunol, v 60, p 53-60, 2003). PlGF is secreted as a glycosylated homodimer.

Recently it has been shown that sFlt-1 and PlGF may be used individually or in combination as biomarkers to predict, diagnose, or monitor pre-eclampsia (Levine et al, NEJM, v 350, p 672-683, 2004).

The amino acid sequence of mature human PlGF-1, amino acid residues 1-132, has been published and is available from the Protein Data Bank identified as PDB 1FZV (Iyer, et al, J. Biol Chem, v 276, p 12153-12161, 2001). This sequence is identified herein as SEQ ID NO:1:

```
MLPAVPPQQW ALSAGNGSSE VEVVPFQEVW GRSYCRALER

LVDVVSEYPS EVEHMFSPSC VSLLRCTGCC GDENLHCVPV

ETANVTMQLL KIRSGDRPSY VELTFSQHVR CECRPLREKM

KPERCGDAVP RR
```

Diagnosis of an individual at risk for, or having pre-eclampsia may be made by determining the presence or amount of vascular endothelial growth factor, particularly PlGF, and/or receptor tyrosine kinase, particularly, sFlt-1 in a biological sample (such as urine, whole blood, serum, plasma, saliva, and so forth) taken from the individual. In analytical assays reference, calibrator and control compositions are essential for purposes of determining the amount or confirming the presence of a target analyte and, for establishing accuracy and precision of the analytical assay. The preparation of such compositions in liquid or dry form usually doesn't present difficulties if the analyte is readily available, soluble in an appropriate solvent—usually aqueous for biological analytes, stable, and does not interact deleteriously with other components that may be present in the composition. As noted above, PlGF binds sFlt-1 to form a stable association complex. As a result compositions comprising the native proteins together in independent amounts suitable for use as a reference, calibrator or control in analytical assays to detect PlGF or sFlt-1 or both PlGF and sFlt-1 cannot be prepared. Although compositions comprising the individual, separated proteins may be prepared it would be advantageous to be able to prepare compositions comprising both proteins together. Thus, a need exists for reference, calibrator or control compositions comprising these proteins together in known and independent amounts. This need has been met with the present invention.

SUMMARY OF THE INVENTION

In one aspect the present invention relates to a composition comprising two or more proteins, one or more of the proteins having been altered to sufficiently reduce or substantially prevent or eliminate mutual recognition and binding. Such a composition is useful as a reference, calibrator or control in analytical assays for one or more of the proteins in the composition.

Considering for clarity two proteins unaltered/native proteins A and B which form a non-covalent association complex, the term "substantially prevent or eliminate their mutual recognition and binding" means that in an assay to determine their mutual binding, binding of altered A to unaltered/native B, or binding of unaltered/native A to altered B, or binding of altered A to altered B is not detectable, or barely detectable, or the mutual affinity as measured quantitatively by determination of affinity constants is less than approximately 10% of that observed for unaltered/native A and unaltered/native B. The term "sufficiently reduce" means that mutual binding occurs, but it has been reduced to a degree that is acceptable for a particular application.

Consider a case where the presence or amount of unaltered or native protein A is to be determined in an analytical assay, which assay utilizes one or more receptors specific for epitopes of protein A. And consider that protein A has been altered to reduce or substantially eliminate binding to protein B. Although protein A has been altered the epitopes remain intact or acceptably intact such that they retain their ability to recognize and bind the receptors. Thereby, altered protein A is acceptable for use in calibrating the assay, confirming the presence of unaltered/native protein A in a sample, or for verifying the accuracy and precision of the assay for unaltered/native protein A. Thus, in general, receptors are capable of recognizing and binding both altered and unaltered/native forms of a protein. Analytical assays comprising receptors are usually immunoassays, which assays employ as receptors polyclonal or monoclonal antibodies, whole, polymeric and/or chimeric forms of antibodies or antibody fragments. Other kinds of receptors are also used, such as aptamers (U.S. Pat. No. 5,840,867; U.S. Pat. No. 6,207,388). In an analytical assay for the determination of unaltered or native protein B using receptors specific for epitopes of protein B, it is not necessary that epitopes of altered protein A remain intact. It is only important that mutual recognition and binding of altered protein A and protein B have been sufficiently reduced or substantially eliminated.

If both protein A and protein B have been altered to reduce or substantially eliminate their mutual recognition and binding then in an analytical assay for determination of unaltered/native protein A or an analytical assay for determining unaltered/native protein B or an analytical assay for determination of both unaltered/native proteins A and B—which assays utilize receptors specific for epitopes of protein A and receptors specific for epitopes of protein B, these epitopes in the altered proteins retain the ability to recognize and bind the receptors used in the assay. Compositions comprising both altered protein A and altered protein B together can then be used for calibrating the assays, confirming the presence of unaltered/native protein A, or unaltered/native protein B, or both unaltered/native protein A and unaltered/native protein B, and for verifying accuracy and precision of the assays.

In another aspect the present invention relates to a reference, calibrator or control composition for use in an assay for a first protein or a second protein or both first and second proteins, wherein one or more amino acids or one or more non-amino acid groups of the first protein or the second protein or the first protein and the second protein have been deleted, modified, or replaced with a different amino acid or non-amino acid group or groups thereby reducing or substantially eliminating mutual binding of the first protein and the second protein.

In another aspect the present invention relates to a composition comprising a receptor tyrosine kinase, preferably fms-like tyrosine kinase, more preferably sFlt-1 and a vascular endothelial growth factor either or both altered, by amino acid or glycosyl deletion, modification or replacement. The vascular endothelial growth factor may be a placental growth factor and preferably, PlGF-1. A preferred composition comprises sFlt-1 and altered PlGF-1 having alanine in place of:
 a) proline at position 25 of SEQ ID NO:1, or
 b) glutamine at position 27 of SEQ ID NO:1, or
 c) cysteine at position 60 of SEQ ID NO:1, or
 d) aspartate at position 72 of SEQ ID NO:1 or
 e) glutamate at position 73 of SEQ ID NO:1, or
 f) asparagine at position 84 of SEQ ID NO:1, or
 g) proline at position 98 of SEQ ID NO:1, or
 h) tyrosine at position 100 of SEQ ID NO:1, or
altered PlGF-1 having glycine in place of cysteine at position 70 of SEQ ID NO:1, or any combination of the alanine replacements in a) to h) and the glycine replacement.

A preferred composition comprises sFlt-1 and altered PlGF-1 having alanine in place of aspartate at position 72 of SEQ ID NO:1 and alanine in place of glutamate at position 73 of SEQ ID NO:1.

Another preferred composition comprises sFlt-1 and altered PlGF-1 having glycine in place of cysteine at position 70 of SEQ ID NO:1, alanine in place of aspartate at position 72 of SEQ ID NO:1, and alanine in place of glutamate at position 73 of SEQ ID NO:1.

In another aspect the present invention relates to a method for calibrating an assay for a protein in a sample comprising the steps of:
 1) contacting a composition as described above comprising known amounts of the protein with a receptor specific for a first epitope of the protein, thereby forming a complex comprising the receptor and the protein of the composition;
 2) contacting the complex formed in step 1) with a labeled receptor specific for a second epitope of the protein, thereby forming a complex comprising receptor, the protein of the composition, and labeled receptor;
 3) detecting a signal from bound labeled receptor or a signal from free labeled receptor; and,
 4) associating the signal from free or bound labeled receptor with the known amounts of the protein in the composition.

In another aspect the invention relates to a method for calibrating an assay for a protein in a sample comprising the steps of:
 1) contacting a composition as described above comprising known amounts of the protein with an immobilized receptor specific for a first epitope of the protein, thereby forming a complex comprising immobilized receptor and the protein of the composition;
 2) contacting the complex formed in step 1) with a labeled receptor specific for a second epitope of the protein, thereby forming a complex comprising immobilized receptor, the protein of the composition and labeled receptor;
 3) separating bound labeled receptor from free labeled receptor;
 4) detecting a signal from bound labeled receptor or a signal from free labeled receptor; and,
 5) associating the signal from free or bound labeled receptor with the known amounts of the protein in the composition.

In yet another aspect the present invention relates to a method for calibrating an assay for a receptor tyrosine kinase and/or a vascular endothelial growth factor in a sample comprising the steps of:
 1) preparing a composition comprising a known or pre-determined amount of the receptor tyrosine kinase and a known or pre-determined amount of the vascular endothelial growth factor either or both altered as described above to reduce or substantially eliminate their mutual recognition and binding;
 2) contacting the composition with a receptor specific for a first epitope of the receptor tyrosine kinase and/or a receptor specific for a first epitope of the vascular endothelial growth factor, thereby forming first complexes of receptor specific for the first epitope of the receptor tyrosine kinase and receptor tyrosine kinase and/or receptor specific for the first epitope of the vascular endothelial growth factor and endothelial growth factor;
 3) contacting complexes formed in step 2) with a labeled receptor specific for a second epitope of the receptor tyrosine kinase and/or a labeled receptor specific for a second epitope of the endothelial growth factor; thereby forming second complexes comprising receptor specific for the first epitope of receptor tyrosine kinase, receptor tyrosine kinase and labeled receptor specific for the second epitope of the receptor tyrosine kinase and/or receptor specific for the first epitope of endothelial growth factor, endothelial growth factor and labeled receptor specific for the second epitope of endothelial growth factor;

4) separating bound labeled receptor specific for receptor tyrosine kinase from free labeled receptor specific for receptor tyrosine kinase and/or bound labeled receptor specific for endothelial growth factor from free labeled receptor specific for endothelial growth factor;

5) detecting a signal from bound labeled receptor specific for receptor tyrosine kinase or a signal from free labeled receptor specific for receptor tyrosine kinase; and/or, 6) detecting a signal from bound labeled receptor specific for endothelial growth factor or a signal from with free labeled receptor specific for endothelial growth factor; and, 7) associating the signal from free or bound labeled receptor specific for receptor tyrosine kinase and/or the signal from free or bound labeled receptor specific for endothelial growth factor with the known amounts of receptor tyrosine kinase and/or endothelial growth factor in the composition.

In a preferred embodiment the receptor tyrosine kinase is sFlt-1 and the endothelial growth factor is PlGF-1, which PlGF-1 has been altered to have alanine in place of:
a) proline at position 25 of SEQ ID NO:1, or
b) glutamine at position 27 of SEQ ID NO:1, or
c) cysteine at position 60 of SEQ ID NO:1, or
d) aspartate at position 72 of SEQ ID NO:1 or
e) glutamate at position 73 of SEQ ID NO:1, or
f) asparagine at position 84 of SEQ ID NO:1, or
g) proline at position 98 of SEQ ID NO:1, or
h) tyrosine at position 100 of SEQ ID NO:1, or
altered PlGF-1 having glycine in place of cysteine at position 70 of SEQ ID NO:1, or any combination of the alanine replacements in a) to h) and the glycine replacement.

In a more preferred embodiment the receptor tyrosine kinase is sFlt-1 and the endothelial growth factor is PlGF-1, which PlGF-1 has been altered to have alanine in place of aspartate at position 72 of SEQ ID NO:1 and alanine in place of glutamate at position 73 of SEQ ID NO:1.

In another more preferred embodiment, the receptor tyrosine kinase is sFlt-1 and the endothelial growth factor is PlGF-1, which PlGF-1 has been altered to have glycine in place of cysteine at position 70 of SEQ ID NO:1, alanine in place of aspartate at position 72 of SEQ ID NO:1, and alanine in place of glutamate at position 73 of SEQ ID NO:1.

In yet another aspect the present invention relates to a method for determining the amount or confirming the presence of a protein in a sample comprising the steps of:
a) contacting the sample with immobilized receptor specific for a first epitope of the protein, thereby forming a first complex comprising immobilized receptor specific for the first epitope of the protein and the protein;
b) contacting the first complex with labeled receptor specific for a second epitope of the protein, thereby forming a second complex of receptor specific for the first epitope of the protein, the protein, and labeled receptor specific for the second epitope of the protein;
c) separating labeled receptor that is bound in the second complex from free labeled receptor;
d) determining a signal from labeled receptor that is bound in the second complex or a signal from free labeled receptor;
e) contacting immobilized receptor specific for the first epitope of the protein with a composition as described above comprising a known or pre-determined amount of the protein, thereby forming a third complex comprising immobilized receptor specific for the first epitope of the protein and the protein of the composition;
f) contacting the third complex with labeled receptor specific for the second epitope of the protein, thereby forming a fourth complex of receptor specific for the first epitope of the protein, the protein of the composition, and labeled receptor specific for the second epitope of the protein;
g) separating labeled receptor that is bound in the fourth complex from free labeled receptor;
h) determining a signal from labeled receptor that is bound in the fourth complex or a signal from free labeled receptor; and,
i) comparing the signals determined in d) and h) as confirmation of the presence of the protein or as a measure of the amount of the protein in the sample.

In a preferred embodiment the protein to be determined is a vascular endothelial growth factor. In a more preferred embodiment the protein to be determined is PlGF and particularly PlGF-1 and the second protein in the composition is a receptor tyrosine kinase. In a more preferred embodiment the protein to be determined is PlGF-1 and the second protein in the composition is sFlt-1. In a more preferred embodiment the protein to be determined is PlGF-1, the second protein in the composition is sFlt-1 and PlGF-1 of the composition has been altered to comprise alanine in place of:
a) proline at position 25 of SEQ ID NO:1, or
b) glutamine at position 27 of SEQ ID NO:1, or
c) cysteine at position 60 of SEQ ID NO:1, or
d) aspartate at position 72 of SEQ ID NO:1 or
e) glutamate at position 73 of SEQ ID NO:1, or
f) asparagine at position 84 of SEQ ID NO:1, or
g) proline at position 98 of SEQ ID NO:1, or
h) tyrosine at position 100 of SEQ ID NO:1, or
altered PlGF-1 having glycine in place of cysteine at position 70 of SEQ ID NO:1, or any combination of the alanine replacements in a) to h) and the glycine replacement.

In a more preferred embodiment the protein to be determined is PlGF-1, the second protein of the composition is sFlt-1 and PlGF-1 of the composition comprises alanine in place of aspartate at position 72 of SEQ ID NO:1 and alanine in place of glutamate at position 73 of SEQ ID NO:1.

In another more preferred embodiment, the protein to be determined is PlGF-1, the second protein of the composition is sFlt-1 and PlGF-1 of the composition comprises glycine in place of cysteine at position 70 of SEQ ID NO:1, alanine in place of aspartate at position 72 of SEQ ID NO:1, and alanine in place of glutamate at position 73 of SEQ ID NO:1.

DETAILED DESCRIPTION

Although the present invention will be described in terms of certain preferred embodiments relating to pre-eclampsia and biomarker proteins sFlt-1 and PlGF-1, it should be understood that the invention relates to any protein composition and its use in which one or more component proteins of the composition have been altered to reduce their mutual recognition and binding.

Whether the pre-eclampsia biomarker proteins are determined using a single assay platform or a single kit, or determined separately in independent assays or kits, it is advantageous to have a control or calibrator comprising both biomarker proteins together in the same formulation having known or pre-determined concentrations and desired concentration ratios. There are at least two problems associated with using sFlt-1 and PlGF together in native or unaltered form to prepare reference, calibrator or control compositions: firstly, sFlt-1 and PlGF bind to each other through a specific binding domain present on each protein, as already noted, and secondly, in the serum of mid- to late-term pregnant women, sFlt-1 is typically present at a significant excess relative to PlGF whether or not they are afflicted with pre-eclampsia. Unmodified or native PlGF combined and stored together with unmodified or native sFlt-1 will not serve satisfactorily in a composition used to calibrate an assay for detection of PlGF or sFlt-1 because of the nearly quantitative binding of PlGF to sFlt-1.

Amino acid changes have been made to PlGF that reduce or substantially eliminate mutual recognition and binding of sFlt-1 and PlGF (Errico et al J. Biol. Chem. 279, 43929-43939, 2004). These amino acid changes do not have a significant impact on the overall protein structure of PlGF. Binding epitopes remain intact and permit these altered proteins to be combined and stored together with sFlt-1 in a composition for use as a reference, calibrator or control for assays designed to detect unaltered or native PlGF, unaltered or native sFlt-1, or both.

Targeting amino acid modifications, deletions or replacements to PlGF in order to reduce or substantially eliminate binding to sFlt-1 has been facilitated because the amino acid sequence of PlGF and 3-D crystal structure are available.

In general it would be advantageous to know secondary, tertiary, and quaternary structures, post-translational modifications (eg phosphorylation, glycosylation, sulfation, and ubiquitination), 3-D crystal structures of binding proteins and 3-D crystal structures of the proteins engaged in their association complex. However, this information is not required in order to practice the present invention. Although modification, deletion or replacement of groups associated with post-translational modifications can be carried out, modification, deletion or replacement of one or more amino acids of one or more of the proteins that engage in mutual recognition and binding is preferred. Site-specific chemical modification of proteins is well known in the art (*Techniques in Protein Modification*, Lundblad R L, CRC Press, 1995; *Chemical Reagents for Protein Modification*, Lundblad, R L, CRC Press, 3$^{rd}$ Ed, 2005). Chemical/synthetic modification of amino acids can be used to practice the present invention. A preferred approach involves genetic engineering techniques. Obtaining the amino acid sequence of a protein directly is standard practice in the art. Similarly, it is standard practice in the art to obtain the amino acid sequence of a protein indirectly from the nucleotide sequence of the gene that codes for the protein. The nucleotide sequence of a gene can be readily obtained. And, when the gene is available site-directed mutagenesis can be carried out to delete, replace, or modify one or more amino acids. This can be done in a random manner or in a predetermined manner. A protein that is altered or mutated using site-directed mutagenesis can be cloned and made readily available. Protein and genetic engineering details and protocols are readily available from numerous publications and citations therein (*Molecular Cloning*, Sambrook J and Russell D W, Cold Spring Harbor Laboratory Press, 2002; *Recombinant Gene Expression Protocols*, Tuan R S ed, Humana Press, 1997; *Methods in Molecular Biology and Protein Chemistry*, Spangler B D, John Wiley & Sons Ltd. 2002; *Genetic Engineering Fundamentals*, Kammermeyer K and Clark V L, Marcel Dekker Inc, 1989; Mayo et al, Nature v 306, p 86-88, 1983; Suggs et al, Proc Nat Acad Sci USA v 78, p 6613-6617 1981; Scott et al Nature v 302, p 538-540, 1983; Helfman et al, Proc Nat Acad Sci USA, v 80, p 31-35, 1983; Young et al, Proc Nat Acad Sci USA, v 80, p 1194-1198, 1983; U.S. Pat. No. 4,237,224; U.S. Pat. No. 4,273,875; U.S. Pat. No. 4,293,652; U.S. Pat. No. 4,870,009).

The altered protein can be tested to determine if mutual recognition and binding with its partner protein(s) have been reduced or substantially eliminated. This can be carried out using experimental protocols well known in the art. The altered protein also can be tested to determine if epitopes have been sufficiently undisturbed compared with unaltered or native protein using epitope specific receptors/antibodies. Affinity can be charac Materials As described by Errico et al., anti-human PlGF monoclonal antibodies and human Flt-1 (Flt-1/Fc chimera) are available from R&D Systems (Minneapolis, Minn. USA). Goat anti-mouse IgG-horseradish peroxidase (HRP) is available from Santa Cruz Biotechnology (Santa Cruz, Calif. USA; www.scbt.com).

Construction of PlGF Variants

Errico et al. obtained PlGF variants using PCR techniques carried out using the plasmid named pchPlGF-1 as template and PCR was performed using complementary primers mapping the region encoding the amino acid to be mutated to alanine and bearing the specific nucleotide modification. For the preparation of the PlGF variant having the double mutation, primers carrying both mutations were utilized. Amplified DNA was purified and used to transform competent bacteria. The plasmids were sequenced in both directions using the dideoxynucleotide method. The following PlGF-1 single residues were mutated to Ala: Asn-16, Pro-25, Gln-27, Cys-60, Asp-72, Glu-73, Asn-74, Asn-84, Pro-98, and Tyr-100. The double mutant Asp 72 to Ala and Glu 73 to Ala of PlGF-1 was also generated.

Calibrator/Control Compositions Comprising Altered PlGF-1

Calibrators/controls comprising altered PlGF-1 and sFlt-1 are prepared by combining unaltered sFlt-1 with an altered PlGF-1, in particular, the double mutant in which alanines replace aspartate at position 72 of SEQ ID NO:1 and glutamate at position 73 of SEQ ID NO:1 or the triple mutant in which there is an additional mutation of glycine replacing cysteine at position 70. These may be combined individually from dry form preparations or from working aqueous stock solutions prepared using any suitable buffer at a desired pH (such as, phosphate in saline (PBS), pH 7.5) comprising any other addenda that may be useful or required—such as antioxidants, preservatives, etc. For illustrative purposes, the concentration of altered PlGF-1 is in the range of 0 to about 1000 pg/mL, and sFlt-1 fixed at 100 pg/mL but other concentration ranges for both may be used. The unaltered sFlt-1 is combined with altered PlGF of the double mutant or the triple mutant in PBS (10 g NaCl, 0.25 g KCl, 1.8 g $Na_2HPO_4$, 0.3 g $KH_2PO_4$, pH 7.5) to produce the following set of reference, calibrator or control materials:

| Altered PlGF1 (pg/mL) | SFlt-1 (pg/mL) |
|---|---|
| 0 | 100 |
| 50 | 100 |
| 100 | 100 |
| 500 | 100 |
| 1000 | 100 |

ELISA For PlGF

The quantity of PlGF in a sample of serum obtained from a pregnant woman is determined using an ELISA for PlGF. The ELISA (described in detail below) is calibrated using the set of solutions comprising altered PlGF-1 and sFlt-1 described above. The signal observed for each PlGF-1 level of the set is associated with the concentration of altered PlGF-1. The association can be represented in graphic form or correlated using appropriate statistical and mathematical calibration methods. The signal observed in the ELISA assay using the serum sample is compared with the calibration graph to determine the concentration of PlGF in the sample or transformed into concentration units using the established mathematical association.

The ELISA is carried out as follows: for determination of PlGF in a sample, one anti-human PlGF-1 monoclonal antibody at 1 µg/ml in PBS is used to coat a 96-well plate at 100 µl/well and incubated overnight at 4° C. The wells are washed once with PBS containing 0.05% TWEEN 20 (PBT) and non-specific binding sites are blocked by introducing 1% bovine serum albumin in PBS at 280 µl/well and incubation for 3 h at room temperature (RT). The wells are aspirated and kept in the cold until use. During the assay, 100 µl of each calibrator level or serum sample is appropriately diluted in PBET (PBS containing 0.1% bovine serum albumin, 5 mM EDTA, 0.05% Tween 20) and incubated for 1 hour at 37° C. The wells are washed five times by PBT and another anti-human PlGF-1 monoclonal antibody (this one HRP conjugated) diluted in PBET at 37 ng/ml, is added to the wells and incubated for 1 h at 37° C. The wells are washed five times with PBT and 100 µl of HRP substrate composed of 1 mg/ml of orthophenylenediamine in 50 mM citrate phosphate buffer, pH 5 and 0.006% $H_2O_2$ is added and incubated for 30 min in the dark at RT. The reaction is stopped by adding 25 µl/well of 4 N $H_2SO_4$, and the signal absorbance is measured at 490 nm on a microplate reader.

Comparison of Altered PlGF-1 and Unaltered PlGF Binding to sFlt-1

Figure 1A:
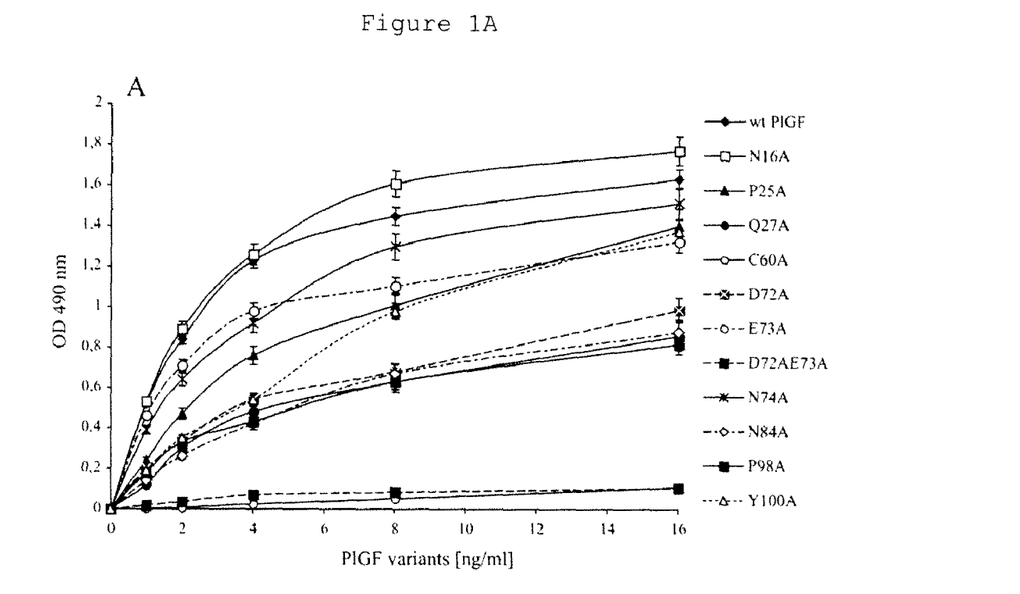
FIG. 1A illustrates ELISA-based binding of PlGF-1 variants to the soluble portion of Flt-1. Binding of PlGF-1 variants to human Flt-1, coated at 0.5 µg/ml on a 96-well plate, was performed using increasing concentrations of soluble proteins ranging between 1 and 16 ng/ml. Wild type PlGF-1 was used as a positive control.
Figure 1B:
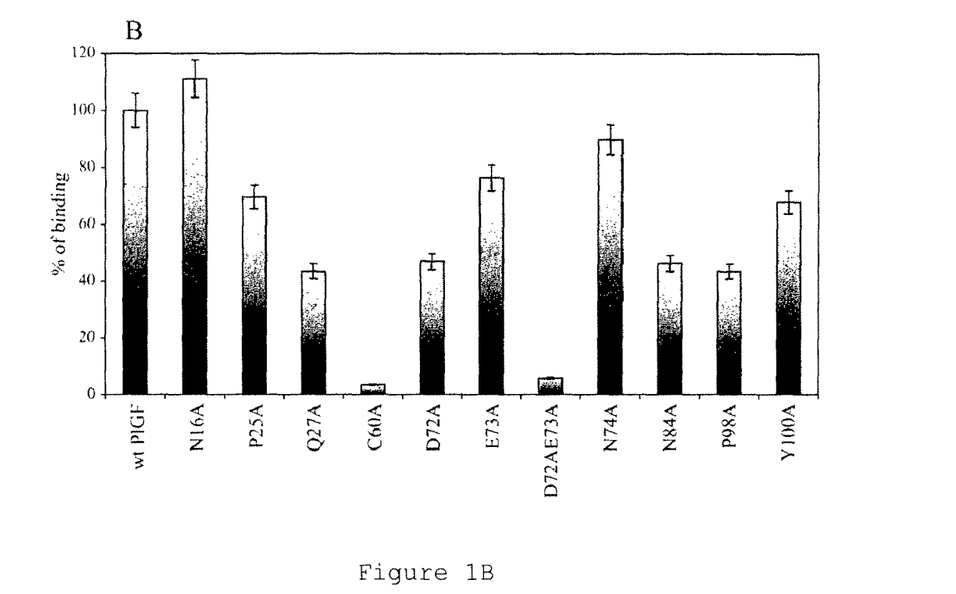
FIG. 1B illustrates ELISA-based binding of PlGF-1 variants to the soluble portion of Flt-1. Percentage of binding of PlGF-1 variants at a concentration of 8 ng/ml calculated with respect to the binding of wt PlGF-1. The results shown represent the average of three independent experiments.

Errico et al. has described the experiment to determine the binding of altered PlGF-1 and unaltered/native PlGF-1 to Flt-1. Basically, a 96-well plate is coated with a soluble human Flt-1 (Flt-1/Fc chimera) at 0.5 µg/ml in PBS, pH 7.5, 100 µl/well, overnight at RT. The plate is washed five times with PBT, and after the blocking non-specific sites of wells with bovine serum albumin solution as described above, the binding reaction is allowed to proceed by adding altered PlGF-1 or unaltered/native PlGF to a well and incubating for 1 h at 37° C. and 1 h at RT. The wells are washed with PBT as described above and incubated with a biotinylated anti-human PlGF-1 polyclonal antibody, 300 ng/ml in PBET, for 1 h at 37° C. and 1 h at RT. Detection is performed as described above in the ELISA assay and the signals obtained with altered PlGF-1 and unaltered/native PlGF-1 are compared. The results obtained by Errico et al. are reproduced in FIG. 1A and FIG. 1B.

Example II

Comparing Recombinant PlGF (DE) and PlGF (AA)

Experiment Purpose:

Two recombinant PlGF proteins were evaluated (1) for their binding reactivity to monoclonal antibody specific to human PlGF, and (2) for their binding reactivity to sFlt, the formation of ligand:receptor complex.

Materials and Reagents:

(1) Recombinant PlGF:

Two versions of purified recombinant PlGF were used. The protein consists of a 21-amino-acid leader sequence that does not belong to PlGF. The leader sequence contains a "6×His" tag and a 4-amino-acid Xa recognition and cleavage site.

```
Leader sequence: SEQ ID NO:2:
MRGSHHHHHHGSGSGSGIEGR
```

The PlGF portion sequence in PlGF (DE): Amino acid sequence corresponds to wild-type PlGF amino acids 4-132 of SEQ ID NO:1, resulting in the following DE amino acid sequence:

SEQ ID NO:3:
AVPPQQWALS AGNGSSEVEV VPFQEVWGRS YCRALERLVD

VVSEYPSEVE HMFSPSCVSL LRCTGCCGDE NLHCVPVETA

NVTMQLLKIR SGDRPSYVEL TFSQHVRCEC RPLREKMKPE

RCGDAVPRR

The PlGF portion sequence in PlGF (AA): Amino acid sequence corresponds to wild-type PlGF amino acids 4-132 of SEQ ID NO:1 with two mutations made at amino acid positions 72 and 73 in SEQ ID NO:1, resulting in the following AA amino acid sequence:

SEQ ID NO:4:
AVPPQQWALS AGNGSSEVEV VPFQEVWGRS YCRALERLVD

VVSEYPSEVE HMFSPSCVSL LRCTGCCGAA NLHCVPVETA

NVTMQLLKIR SGDRPSYVEL TFSQHVRCEC RPLREKMKPE

RCGDAVPRR (2) Recombinant sFlt:

Full length sFlt was obtained from Scios Inc. (Mountain View, Calif. USA; www.sciosinc.com) (Lot#9225-89), consists of 687 amino acids of soluble fms-like tyrosine kinase 1 (sFlt-1).
sFlt-1 sequence:

SEQ ID NO:5:
MVSYWDTGVLLCALLSCLLLTGSSSGSKLKDPELSLKGTQHIMQAGQTLH

LQCRGEAAHKWSLPEMVSKESERLSITKSACGRNGKQFCSTLTLNTAQAN

HTGFYSCKYLAVPTSKKKETESAIYIFISDTGRPFVEMYSEIPEIIHMTE

GRELVIPCRVTSPNITVTLKKFPLDTLIPDGKRIIWDSRKGFIISNATYK

EIGLLTCEATVNGHLYKTNYLTHRQTNTIIDVQISTPRPVKLLRGHTLVL

HYSISKQKMAITKEHSITLNLTIMNVSLQDSGTYACRARNVYTGEEILQK

KEITIRGEHCNKKAVFSRISKFKSTRNDCTTQSNVKH (3) Monoclonal Antibody to Human sFlt-1 and to Human PlGF:

| monoclonal Ab ID | Source | Cat # | Lot | Clone |
|---|---|---|---|---|
| RD-1 mouse anti-sFlt | RD Sys | | CGG07605B | 49560 |
| RD-2 mouse anti-sFlt | RD Sys | | BYC01605A | 49543 |
| Rat-1 rat anti-PlGF | RD Sys | n/a | 1103925 | 358903 |
| Rat-2 rat anti-PlGF | RD Sys | n/a | 1103933 | 358939 |
| Rat-3 rat anti-PlGF | RD Sys | n/a | 1103931 | 358932 |
| Rat-4 rat anti-PlGF | RD Sys | n/a | 1103926 | 358905 |
| Rat-5 rat anti-PlGF | RD Sys | n/a | 1103927 | 358907 |
| MS-1 mouse anti-PlGF | RD Sys | MAB264 | n/a | 37203 |

Experiment Examples:

(1) ELISA Assay-1:

High-binding microtiter plate was coated with recombinant PlGF(DE) or PlGF(AA) at 0.5 ug/mL and blocked with BSA/PBS Standard ELISA procedure consists of monoclonal antibody dilution in casein/PBS; dilution of HRP conjugated donkey anti-mouse IgG or donkey anti-rat IgG at 1:3K in casein/PBS; 100 uL/well sample or conjugate volume; each step incubation at 37 C/30 min/shake; 6 times plate washing, 100 uL OPD substrate development for 25 C/30 min; 25 uL stop solution; record OD at 492 nm.

ELISA results assay 1 are shown in Table 1.

TABLE 1

Recognition of monoclonal anti-PlGF to recombinant PlGF (unaltered and altered)

| Coated recombinant | Antibody binding activity to coated PlGF (OD) Monoclonal anti-PlGF ID, clone # and concentration (ng/mL) | | | | | | |
|---|---|---|---|---|---|---|---|
| PlGF (0.5 µg/mL) | | Ms-1 37203 | Rat1 358903 | Rat2 358939 | Rat4 358905 | | Rat3 358932 | Rat5 358907 |
| PlGF-1 (DE) | Ab | 1.823 | 2.098 | 2.237 | 2.114 | Ab | 1.233 | 1.256 |
| PlGF-1 (AA) | (10 ng/mL) | 2.650 | 1.789 | 2.233 | 1.935 | (100 ng/mL) | 1.305 | 1.297 |

-continued

NCTATTPLNTRVQMTWSYPDEKNKRASVRRRIDQSNSHANIFYSVLTIDK

MQNKDKGLYTCRVRSGPSFKSVNTSVHIYDKAFITVKHRKQQVLETVAGK

RSYRLSMKVKAFPSPEVVWLKDGLPATEKSARYLTRGYSLIIKDVTEEDA

GNYTILLSIKQSNVFKNLTATLIVNVKPQIYEKAVSSFPDPALYPLGSRQ

ILTCTAYGIPQPTIKWFWHPCNHNHSEARCDFCSNNEESFILDADSNMGN

RIESITQRMAIIEGKNKMASTLVVADSRISGIYICIASNKVGTVGRNISF

YITDVPNGFHVNLEKMPTEGEDLKLSCTVNKFLYRDVTWILLRTVNNRTM

Conclusion: All monoclonal antibodies tested reacted to both PlGF(DE) and PlGF(AA), indicating that D72/E73A mutation did not affect monoclonal antibody binding and these antibody epitope locations were not at these two mutation sites.

(2) ELISA Assay-2:

High-binding microtiter plate was coated with recombinant PlGF(DE) or PlGF(AA) at 0.5 ug/mL and blocked with BSA/PBS Standard ELISA procedure consists of 1st plate incubation with diluted sFlt in casein/PBS at various concentrations; 2nd plate incubation with mixed anti-sFlt solution comprising two monoclonal antibodies of RD-1 and RD-2 each at 0.1 µg/mL; 3rd plate incubation with HRP conjugated donkey anti-mouse at IgG at 1:4K dilution in casein/PBS; and 4th plate incubation with 100 μL OPD substrate development for 30 min at 25° C. 1st, 2nd and 3rd plate incubation steps are for 15-20 min/shake at 37° C.; 6 times plate washing between each step. 25 μL stop solution after 4th incubation and record OD at 492 nm.

ELISA results assay-2 are shown in Table 2.

TABLE 2

Binding of sFlt to recombinant PlGF (unaltered and altered)

| Coated recombinant PlGF | Complex formation of sFlt to coated PlGF sFlt concentration (ng/mL) at incubation | | | |
|---|---|---|---|---|
| (0.5 μg/mL) | 1800 | 600 | 200 | 66.67 |
| BSA (control) | 0.004 | 0.006 | 0.010 | 0.020 |
| PlGF-1 (DE) | 1.728 | 1.204 | 0.524 | 0.316 |
| PlGF-1 (AA) | 0.150 | 0.080 | 0.060 | 0.040 |

* Bound sFlt:PlGF complex were detected by mouse anti-sFlt and HRP anti-mouse conjugate Conclusion: sFlt formed receptor:ligand complex with coated PlGF(DE). However, such complex formation was greatly reduced with PlGF(AA) mutant, indicating that amino acid positions 72 and 73 in SEQ ID NO:1 were critical for sFlt-1 binding and complex formation.

(3) Biacore Assay:

sFlt were immobilized on Biacore chip FC-2 via NHS/EDC coupling to a RU=6738. FC-1 was blank as negative control.

PlGF(DE) or PlGF(AA) were injected to FC-1 and FC-2 to evaluate complex formation Biacore results are shown in Table 3.

TABLE 3

Biacore measurement of sFlt:PlGF complex

| CM5 Chip: | | recomb hu P1GF 20 μg/mL | |
|---|---|---|---|
| | | PlGF (DE) | PlGF (AA) |
| Bicore (RU) | FC1: blank | 11 | 12 |
| | FC2: sFlt | 156 | 30 |
| | FC2 − FC1 | 145 | 18 |

Conclusion: Injected PlGF(DE) bound to immobilized sFlt to form receptor:ligand complex while injected PlGF (AA) bound to immobilized sFlt poorly.

Example III

Comparison Between Wild-Type Recombinant PlGF and Two Additional PlGF Mutants

Experiment Purpose:

Three additional recombinant PlGF proteins were constructed and evaluated (1) for their binding reactivity to monoclonal antibody specific to human PlGF, and (2) for their binding reactivity to sFlt, the formation of ligand:receptor complex.

Materials and Reagents:

(1) Three additional recombinant PlGF proteins were constructed as follows:

P126(DE): recombinant P1GF wild type: SEQ ID NO:6:
MRGSAVPBQQWALSAGNGSSEVEVVPFQEVWGRSYCRALERLVDVVSEYP

SEVEHMFSPSCVSLLRCTGCCGDENLHCVPVETANVTMQLLKIRSGDRPS

YVELTFSQHVRCECRPLREKMKPERCGDAVGPGQIVGGVYLL

The first four amino acid residues are unrelated amino acids (MRGS); the last ten amino acids are the 10 G epitope (C terminal tag); the two amino acids preceding the 10 G epitope are also unrelated amino acids (Gly-Pro); the 126 amino acid sequence between the unrelated amino acids (i.e. beginning after MRGS and preceding GP) is the PlGF sequence identical to amino acid positions 4 to 129 in SEQ ID NO:1.

P126(AA): P1GF mutant #1: SEQ ID NO:7:
MRGSAVPPQQWALSAGNGSSEVEVVPFQEVWGRSYCRALERLVDVVSEYP

SEVEHMFSPSCVSLLRCTGCCAANLHCVPVETANVTMQLLKIRSGDRPS

YVELTFSQHVRCECRPLREKMKPERCGDAVGPGQIVGGVYLL same as P126(DE) except the underlined amino acids (AA) are the two mutated amino acids P126(GAA): P1GF mutant #2: SEQ ID NO:8:
MRGSAVPPQQWALSAGNGSSEVEVVPFQEVWGRSYCRALERLVDVVSEYP

SEVEHMFSPSCVSLLRCTGCGAANLHCVPVETANVTMQLLKIRSGDRPS

YVELTFSQHVRCECRPLREKMKPERCGDAVGPGQIVGGVYLL same as PlGF mutant#1 P126(AA) except an additional mutation at the amino acid two before AA is mutated from C to G All three recombinant proteins were expressed in bacteria and all form insoluble inclusion bodies. After sonication, washing with 4 M urea in PBS and 2M urea in PBS, inclusion bodies were finally solubilized by 8M urea/15 mM reduced Glutathione (GSH)/50 mM Tris-HCL (pH7.8). PlGF proteins were refolded through three step dialysis: (1) 24 hours against dialysis buffer 3M urea/50 mM TRIS (pH7.5)/2 mM EDTA/0.2 M Arginine/2 mM GSH, (2) 24 hours against dialysis buffer 2M urea/50 mM TRIS (pH7.5)/2 mM EDTA/0.2 M Arginine/1.2 mM GSH/0.4 mM oxidized Glutathione (GSSG) and (3) 24 hours against dialysis buffer 0.8M urea/20 mM TRIS (pH7.5)/2 mM EDTA/0.2 M Arginine/0.48 mM GSH/0.16 mM GSSG. Refolded PlGF were further purified by loading dialyzed protein solution to an affinity column, prepared by cross linking monoclonal antibody specific to 10 G tag and CNBr-activated Sepharose 4 Fast Flow resin (GE catalogue #17-0981-01). The bound PlGF was then eluted by 40% acetonitrile. Purified PlGF proteins were finally obtained after buffer exchange to PBS.

(2) Monoclonal anti-human PlGF, monoclonal anti-human sFlt are available from R&D Systems (Minneapolis, Minn. USA); HRP conjugated donkey anti-rat IgG (Cat#712-035-150) are available from Jackson ImmunoResearch Laboratories, Inc. (West Grove, Pa., USA); ELISA plates were Costar hind binding by Corning Life Sciences (Cat#2592); Electrophoresis gels NuPAGE 4-12%, PVDF transfer membrane and SeeBlue ladder were from Invitrogen (Carlsbad Calif., USA); Blocker casein/PBS and SuperSignal West Dura western blot substrate were purchased from Pierce (Rockford, Ill., USA).

CNBr-activated Sepharose 4 Fast Flow resin (Cat #17-0981-01) and Silver stain kit (Cat #17-1150-01) were from GE Healthcare (Piscataway, N.J., USA)

Figure 2:
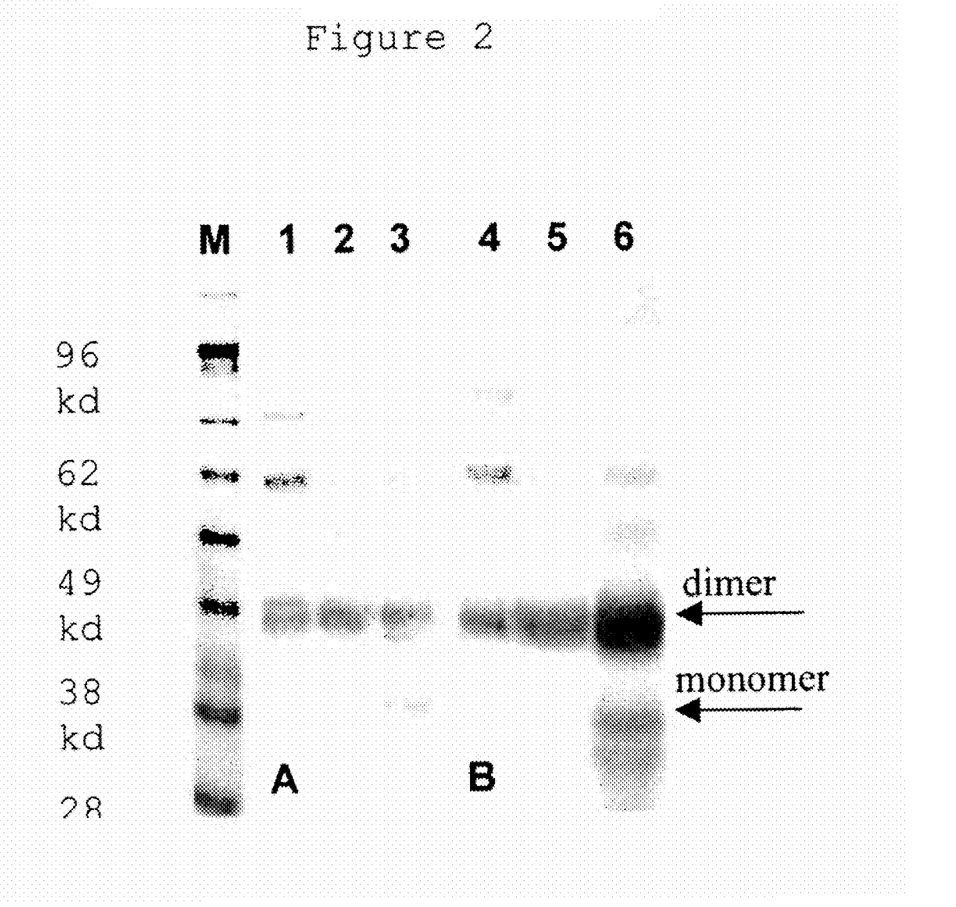
FIG. 2 illustrates the purity of three PlGF recombinant proteins. Silver stain (A: lanes 1, 2 and 3) and Western blot by monoclonal Rat-4 (B: lanes 4, 5 and 6). Lane assignment: M: SeaBlue ladder (Invitrogen), lane 1,4-P126(DE), lane 2,5-P126(AA) and lane 3,6-P126(GAA).

Experiment Examples:
(1) Recombinant PlGF: FIG. 2 Shows the Purity of the Three PlGF Recombinant Proteins by Silver Stain and Western Blot.
(2) ELISA Assay-1
  High-binding microtiter plate was coated with recombinant P126(DE) or P126(AA) or P126(GAA) at 0.5 ug/mL and blocked with BSA/PBS
  Standard ELISA procedure consists of monoclonal antibody dilution in casein/PBS; dilution of HRP conjugated donkey anti-mouse IgG or donkey anti-rat IgG at 1:3K in casein/PBS; 100 uL/well sample or conjugate volume; each step incubation at 37 C/30 min/shake; 6 times plate washing, 100 uL OPD substrate development for 25 C/30 min; 25 uL stop solution; record OD at 492 nm.
  ELISA results are shown in Table 4.

TABLE 4

Recognition of monoclnal anti-PlGF to recombinant PlGF (unaltered and altered)

| Coated recombinant PlGF (0.5 ug/mL) | | Antibody binding activity to coated PlGF (OD) Monoclonal anti-PlGF ID, clone # and concentration (ng/mL) | | | | | | |
|---|---|---|---|---|---|---|---|---|
| | | Ms-1 37203 | Rat1 358903 | Rat2 358939 | Rat4 358905 | | Rat3 358932 | Rat5 358907 |
| P126 (DE) | Ab at | 1.023 | 1.368 | 1.497 | 1.634 | Ab at | 0.779 | 0.834 |
| P126 (AA) | 1 ng/mL | 0.967 | 1.301 | 1.633 | 1.681 | 10 ng/mL | 0.681 | 0.697 |
| P126 (GAA) | | 1.134 | 1.226 | 1.530 | 1.591 | | 0.806 | 0.799 |

Conclusion: All monoclonal antibodies tested reacted to P126(DE), P126(AA) and P126(GAA), indicating that D72A/E73A double mutation and C70G/D72A/E73A triple mutation did not affect monoclonal antibody binding and these antibody epitope locations were not at these mutation sites.

(3) ELISA Assay-2:
  High-binding microtiter plate was coated with recombinant P126(DE), P126(AA) and P126(GAA) at 0.5 ug/mL and blocked with BSA/PBS
  Standard ELISA procedure consists of $1^{st}$ plate incubation with diluted sFlt in casein/PBS at various concentration, $2^{nd}$ plate incubation with mixed anti-sFlt solution comprising two monoclonal antibodies of RD-1 and RD-2 each at 0.1 ug/mL, $3^{rd}$ plate incubation with HRP conjugated donkey anti-mouse IgG at 1:4K dilution in casein/PBS and $4^{th}$ plate incubation with 100 uL OPD substrate development for 25 C/30 min. $1^{st}$, $2^{nd}$ and $3^{rd}$ plate incubation step is at 37 C/15-20 min/shake; 6 times plate washing between each step. 25 uL stop solution after $4^{th}$ incubation and record OD at 492 nm.
  ELISA results are shown in Table 5.

TABLE 5

Binding of sFlt to recombinant PlGF (unaltered and altered)

| Coated recombinant | Complex formation of sFlt to coated PlGF sFlt concentration (ng/mL) at incubation | | | |
|---|---|---|---|---|
| PlGF at (5 ug/mL) | 1800 | 600 | 200 | 66.67 |
| BSA (control) | 0.009 | 0.008 | 0.005 | 0.003 |
| P126 (DE) | >3 | 1.833 | 0.833 | 0.347 |

TABLE 5-continued

Binding of sFlt to recombinant PlGF (unaltered and altered)

| Coated recombinant | Complex formation of sFlt to coated PlGF sFlt concentration (ng/mL) at incubation | | | |
|---|---|---|---|---|
| PlGF at (5 ug/mL) | 1800 | 600 | 200 | 66.67 |
| P126 (AA) | 0.210 | 0.182 | 0.115 | 0.143 |
| P126 (GAA) | 0.150 | 0.101 | 0.095 | 0.088 |

* Bound sFlt:PlGF complex were detected by mouse anti-sFlt and HRP anti-mouse conjugate Conclusion: sFlt formed receptor:ligand complex with coated P126(DE). However, such complex formation was greatly reduced with P126(AA) mutant and P126(GAA) mutant, indicating that amino acid position 70, 72 and 73 in SEQ ID NO:1 were critical for sFlt-1 binding and complex formation.

(4) ELISA Assay-3:
  High-binding microtiter plate was coated with recombinant sFlt at 0.5 ug/mL and blocked with BSA/PBS
  Standard ELISA procedure consists of $1^{st}$ plate incubation with diluted P126(DE) or P126(AA) or P126(GAA) in casein/PBS at various concentration, $2^{nd}$ plate incubation with monoclonal anti-PlGF Rat-4 solution at 0.1 ug/mL, $3^{rd}$ plate incubation with HRP conjugated donkey anti-Rat IgG at 1:4K dilution in casein/PBS and $4^{th}$ plate incubation with 100 uL OPD substrate development for 25 C/30 min. $1^{st}$, $2^{nd}$ and $3^{rd}$ plate incubation step is at 37 C/15-20 min/shake; 6 times plate washing between each step. 25 uL stop solution after $4^{th}$ incubation and record OD at 492 nm.
  ELISA results are shown in Table 6.

TABLE 6

Binding of recombinant PlGF (unaltered and

| Coated | Complex formation of PlGF (unaltered or altered) to PlGF (ng/mL) at | | | | |
|---|---|---|---|---|---|
| sFlt at (0.5 | 1000 | 500 | 250 | 100 | 0 |
| P126 (DE | >3 | 1.388 | 0.557 | 0.259 | 0.021 |
| P126 (A | 0.299 | 0.118 | 0.101 | 0.077 | 0.009 |
| P126 (GA | 0.119 | 0.117 | 0.069 | 0.088 | 0.051 |

* Bound sFlt:PlGF complex were detected by mouse anti-PlGF (Rat-4) and conjugat

Conclusion: unaltered PlGF, P126(DE), formed ligand:receptor complex with coated sFlt. However, altered PlGF (P126(AA) and P126(GAA) failed to form such complex, indicating that amino acid position 70, 72 and 73 in SEQ ID No:1 were critical for sFlt binding and complex formation.

The description of the specific embodiments of the invention is presented for the purposes of illustration. It is not intended to be exhaustive or to limit the scope of the invention to the specific forms described herein. It will be understood by one of ordinary skill in the art that various modifications can be made without departing from the spirit and scope of the invention as set forth in the claims.

All patents, patent applications, and publications cited herein are hereby incorporated by reference.

We claim:

1. A reference, calibrator or control composition comprising PlGF-1 and sFlt-1, where the PlGF-1 comprises alanine in place of:

a) proline at position 25 of SEQ ID NO:1, or
b) glutamine at position 27 of SEQ ID NO:1, or
c) cysteine at position 60 of SEQ ID NO:1, or
d) aspartate at position 72 of SEQ ID NO:1 or
e) glutamate at position 73 of SEQ ID NO:1, or
f) asparagine at position 84 of SEQ ID NO:1, or
g) proline at position 98 of SEQ ID NO:1, or
h) tyrosine at position 100 of SEQ ID NO:1, or altered PlGF-1 having glycine in place of cysteine at position 70 of SEQ ID NO:1, or any combination of the alanine replacements in a) to h) and the glycine replacement.

2. The composition of claim 1 wherein PlGF-1 comprises alanine in place of aspartate at position 72 of SEQ ID NO:1 and alanine in place of glutamate at position 73 of SEQ ID NO:1.

3. The composition of claim 1 wherein PlGF-1 comprises glycine in place of cysteine at position 70 of SEQ ID NO:1, alanine in place of aspartate at position 72 of SEQ ID NO:1 and alanine in place of glutamate at position 73 of SEQ ID NO:1.

* * * * *